United States Patent
Zavrel et al.

(10) Patent No.: US 10,316,341 B2
(45) Date of Patent: *Jun. 11, 2019

(54) PROCESS FOR THE HYDROLYSIS OF LIGNOCELLULOSIC MATERIAL, WHEREIN THE HYDROLYSATE IS USED FOR MICROBIAL HYDROLASE PRODUCTION

(71) Applicant: CLARIANT INTERNATIONAL LTD., Muttenz (CH)

(72) Inventors: Michael Zavrel, Olching (DE); Danielle Dennewald, Munich (DE); Joerg Bartuch, Munich (DE); Henning Marckmann, Buchloe (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,206

(22) PCT Filed: May 20, 2015

(86) PCT No.: PCT/EP2015/061072
§ 371 (c)(1),
(2) Date: Nov. 18, 2016

(87) PCT Pub. No.: WO2015/177189
PCT Pub. Date: Nov. 26, 2015

(65) Prior Publication Data
US 2017/0081687 A1    Mar. 23, 2017

(30) Foreign Application Priority Data
May 21, 2014 (EP) .................................. 14001784

(51) Int. Cl.
| | | |
|---|---|---|
| C12P 19/02 | (2006.01) | |
| C12P 19/14 | (2006.01) | |
| C12N 9/42 | (2006.01) | |
| C12P 19/28 | (2006.01) | |
| C12N 9/24 | (2006.01) | |
| C12P 5/02 | (2006.01) | |
| C12P 7/02 | (2006.01) | |
| C12P 7/40 | (2006.01) | |
| C12P 7/64 | (2006.01) | |
| C12P 13/04 | (2006.01) | |
| C12P 17/10 | (2006.01) | |

(52) U.S. Cl.
CPC .............. *C12P 19/02* (2013.01); *C12N 9/24* (2013.01); *C12N 9/2437* (2013.01); *C12N 9/2445* (2013.01); *C12P 5/023* (2013.01); *C12P 7/02* (2013.01); *C12P 7/40* (2013.01); *C12P 7/649* (2013.01); *C12P 13/04* (2013.01); *C12P 17/10* (2013.01); *C12P 19/14* (2013.01); *C12P 19/28* (2013.01); *C12Y 302/01004* (2013.01); *C12Y 302/01021* (2013.01); *C12P 2201/00* (2013.01); *Y02E 50/13* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 2014/0170723 A1* | 6/2014 | Dobson | ..................... | C12P 7/10 435/165 |
| 2014/0356915 A1* | 12/2014 | Retsina | ..................... | C12P 7/40 435/109 |

FOREIGN PATENT DOCUMENTS

WO    WO2014202623    * 12/2014

OTHER PUBLICATIONS

Jin et al. Biotechnol Bioeng. May 2013;110(5):1302-11.*
Ito et al. Biosci Biotechnol Biochem. 2014;78(1):151-9. Epub Apr. 14, 2014.*
Casey et al. Biotechnol Biofuels. May 29, 2013;6(1):83.*
Jørgensen et al. Biotechnol Bioeng. Apr. 1, 2007;96(5):862-70.*
Ju, L., et al.; Wastepaper Hydrolysate as Soluble Inducing Substrate for Cellulase Production in Continuous Culture of Trichoderma reesei; Biotechnol. Program 1999, vol. 15, pp. 91-97.
Palmqvist, E., et al.; Simultaneous detoxification and enzyme production of hemicellulose hydrolysates obtained after steam pretreatment; Enzyme and Microbial Technology, 1997, vol. 20, pp. 286-293.
Wyman, C., et al.; Hydrolysis of Cellulose and Hemicellulous; Copyright 2005 by Marcel Dekker.
Jourdier, E., et al.; Comprehensive Study and Modeling of Acetic Acid Effect on Trichoderma reesei Growth; Industrial Biotechnology, Jun. 2013, vol. 9, No. 3, pp. 132-138.
T. Foyle et al., "Compositional analysis of lignocellulosic materials: Evaluation of methods used for sugar analysis of waste paper and straw", Bioresource Technology, (2007), vol. 98, pp. 3026-3036.
Brown, D.E., "Lignocellulose hydrolysis", Phil. Trans. Soc. Lond. B 300, 305-322 (1983).
Gustafson, R., et al., "Converting Washington Lignocellulosic Rich Urban Waste to Ethanol", University of Washington, The Washington State Department of Ecology (2007-2009).
Hadar, Y., "Sources for Lignocellulosic Raw Material for the Production of Ethanol", V. Faraco (ed.), Lignocellulose Conversion, DOI: 10.1007/978-3-642-37861-4_2, © Springer-Verlag Berlin Heidelberg 2013.

\* cited by examiner

*Primary Examiner* — Christian L Fronda
(74) *Attorney, Agent, or Firm* — Arent Fox LLP

(57) ABSTRACT

The present invention is directed to a process for self-sufficient hydrolysis of lignocellulosic material. In an additional aspect, the present invention is directed to a process for the production of an organic product and the organic product produced according to this process.

14 Claims, 2 Drawing Sheets

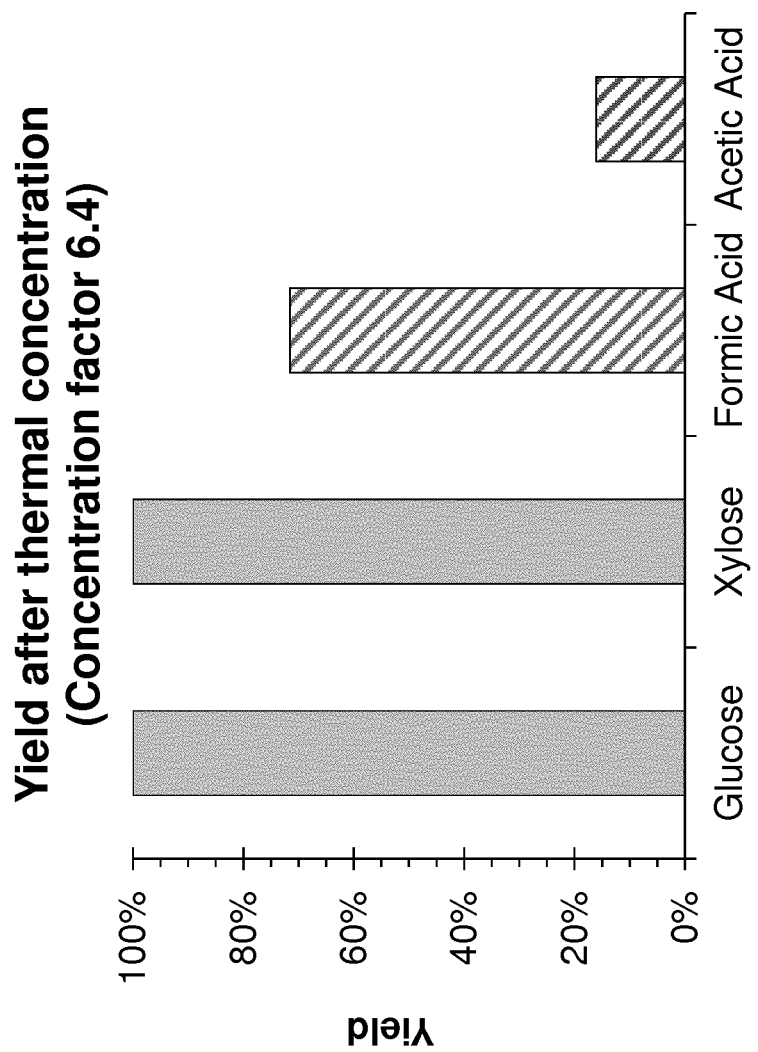

PROCESS FOR THE HYDROLYSIS OF LIGNOCELLULOSIC MATERIAL, WHEREIN THE HYDROLYSATE IS USED FOR MICROBIAL HYDROLASE PRODUCTION

CROSS REFERENCE TO RELATED APPLICATIONS

This application claims the priority of PCT/EP2015/061072, filed on 20 May 2015, which claims priority to European Patent Application No. 14001784.9, filed 21 May 2014, the entire contents of each of which are hereby incorporated in total by reference.

The present invention is directed to a process for self-sufficient hydrolysis of lignocellulosic material. In an additional aspect, the present invention is directed to a process for the production of an organic product and the organic product produced according to this process.

Due to limited resources of mineral oil and demands to reduce $CO_2$ emissions the chemical industry seeks more sustainable production routes for the manufacture of commodity chemicals such as liquid fuels and base chemicals. Part of that strategy focusses on the conversion of lignocellulosic biomass into versatile chemicals or fuels such as ethanol. Lignocellulosic biomass contains cellulose (~25-40% w/w d.s.), hemicellulose (~15-25% w/w d.s.) and lignin (~15-30% w/w d.s.) as major components and minor amounts of other carbohydrates, waxes, proteins and inorganic compounds. Among forms of plant biomass, lignocellulosic biomass derived from any forestry and agricultural waste streams, such as wood residues and cereal straw are particularly well suited for conversion to commodity chemicals and fuels because of their availability, low cost and environmentally sound production. Additionally, life cycle analyses of production processes utilising lignocellulosic feedstocks indicate reduced greenhouse gas emissions compared to processes based on other feedstocks.

Various process options that describe the conversion of lignocellulosic biomass to ethanol and other base chemicals have been described (Pejo et al., 2008). To realize these processes on an industrial scale it is particularly desirable to transfer the maximal amount of energy, carbon and mass content contained in the renewable feedstock to the end products. At present none of the described conversion processes have realised this to the full extent.

Exemplary unit operations for the biotechnological conversion of lignocellulosic material (e.g. straw) to value-adding products (e.g. ethanol) are: mechanical de-sizing and/or physicochemical pretreatment, enzymatic hydrolysis, fermentation and product recovery. To ascertain maximum process efficiency it is mandatory to convert a maximum amount of polysaccharides into soluble sugars during the enzymatic hydrolysis unit.

Regarding industrial scale cellulosic ethanol production, the key barrier is still the expenditure for cost for efficient enzymatic hydrolysis of pre-treated lignocellulose at high solids concentrations.

Thus, the hydrolysis of the cellulose fraction has been identified as one of the main obstacles in conversion of lignocellulose to ethanol. At present enzyme cost and performance required for efficient biomass hydrolysis are the major bottlenecks.

Decomposition of the pre-treated biomass slurry into fermentable monomeric sugars can be accomplished by either acid or enzyme catalysed hydrolysis. The enzymatic hydrolysis is more selective and less energy intense than comparable chemical (such as acid-based) methodologies, therefore providing more favourable process economics and potentially a higher ethanol yield during fermentation.

Suitable enzyme systems that convert polymeric sugars such as cellulose and hemicellulose into hexose (i.e. glucose) and pentose (i.e. xylose) monomers typically contain cellulase, hemicellulase and beta-glucosidase activities. Enzyme systems containing cellulase and beta-glucosidase activities are often produced in submerged liquid cultures of fungi, e.g. *Trichoderma* sp. and/or *Aspergillus* sp. Residue of fungal biomass is usually separated from the fermentation broth and discarded. The fermentation broth is then concentrated, stabilised and formulated for the resulting enzyme product to be shipped.

According to Kristensen et al. (2009) enzymatic hydrolysis of biomass is often conducted at a lower solids content of 10-20% w/w. A solid content above 15% w/w often leads to significant losses in monomeric sugar yields. This effect is due to problems associated with homogenous mixing of high solid content slurries leading to uneven enzyme distribution. In addition, accumulation of end products like cellobiose and glucose released during enzymatic hydrolysis can lead to inherent inhibition of cellulase and beta-glucosidase activities (Xiao et al., 2004a).

Rao et al. (1985) indicate the utilisation of the entire fungal fermentation slurry for efficient hydrolysis of cellulose substrates. However, artificial media were used for enzyme production, which do not allow tailoring the hydrolysis enzyme production to a specific feedstock and/or pre-treatment option and therefore efficiency of the enzyme production is rather low. Tolan (Clean Techn Environ Policy 3 (2002) 339-345) describes in "Iogen's process for producing ethanol from cellulosic biomass" the use of crude broth from the hydrolysis as medium for enzyme production to save process costs. Another drawback of the methods disclosed by Rao et al. and Tolan is the limitation to secreted enzymatic activities, because nothing is undertaken to facilitate release of non-secretory or cell-surface bound enzymes.

The aforementioned conventional techniques for degradation of biomass are either inefficient or depend on time- and cost-consuming addition of commercial, separately produced enzymes or enzyme mixtures which are appropriate for the degradation of the specific biomass. Further, also the use of crude slurry or broth does not overcome these drawbacks, as it leads not only to the desired provision of the necessary sugars for fungal fermentation, but will inevitably also import a variety of non-desired inhibitory and/or toxic substances to the fermentation process. Thus the advantage of using a cheap fermentation medium will be offset by a severe drawback in efficiency regarding enzyme production.

Within the EP 2 471 940 an efficient lignocellulose hydrolysis process with integrated enzyme production was described. In this process the media for enzyme fermentation consists of high amounts of suspended solids. To further improve economics, the aim of the invention is to develop a lignocellulose hydrolysis and enzyme fermentation process with a minimized amount of suspended solids and inhibitors, whereas the amount of soluble carbohydrates is further increased.

Therefore, the object of the present invention is the provision of an improved highly efficient process for degradation of biomass, such as lignocellulosic biomass.

The inventors of the present invention have now surprisingly found that this object of the present invention may be achieved by a process for self-sufficient enzymatic hydrolysis of lignocellulose-containing material, comprising the steps (a) subjecting a lignocellulose-containing material to a pretreatment in a pretreatment device;
(b) contacting the pretreated lignocellulose-containing material of step a) with at least one enzyme belonging to the class of hydrolases in a hydrolysis vessel to form a hydrolyzate;
(c) separating the hydrolyzate and subsequently dividing the hydrolyzate into two parts (i) and (ii), wherein part (i) is directed to a cultivation vessel;
(d) fermenting part (i) of the hydrolyzate with at least one microorganism and/or fungus capable of the production of at least one enzyme belonging to the class of hydrolases; and
(e) redirecting the fermented hydrolyzate of step d) to the hydrolysis vessel of step b);
wherein the pretreated lignocellulose-containing material and/or hydrolyzate is treated to remove at least one substance inhibitory to at least one enzyme and/or at least one microorganism and/or fungus.

The process for enzymatic hydrolysis of lignocellulose-containing material of the present invention is particularly advantageous as it is self-sufficient but also highly efficient as integrating hydrolyzate of the all-over process within the enzyme production step (d) will enable an economical production and direct on-site integration of a maximum amount of suitable hydrolytic enzymes leading to a maximum amount of soluble carbohydrates. Further, removal of inhibitory substances during at least one process stage will enable a process which can not only be run self-sufficient but also continuously with high efficiency as hydrolytic enzyme production will not be slowed down or inhibited by undesired substances leading to further economical advantages.

Within the present invention the term "lignocellulose-containing material" is to be understood to comprise all kind of material known to a person skilled in the art as comprising lignocellulose. Terms "lignocellulose-containing material", "lignocellulose-containing biomass", "lignocellulosic material" and "lignocellulosic biomass" are to be understood as synonyms within the present invention. Particularly preferred lignocellulose-containing material according to the present invention include wood, cereal straw and/or husks, bagasse, oat hulls, switch grass, cellulose, raw paper pulp (obtained from pulp and paper production) and mixtures thereof. Alternative sources or additional components may comprise one or more of the following components: purified cellulose, pulp, milk whey, molasses or sugars such as glucose and lactose. In a preferred embodiment the lignocellulose-containing material contains at least 25 wt.-%, preferably at least 40 wt.-%, more preferably at least 70 wt.-%, even more preferably at least 80 wt.-% and most preferred at least 90 wt.-% lignocellulose. It is to be understood that the lignocellulose-containing material may also comprise other compounds such as proteinaceous material, starch, sugars, such as fermentable sugars and/or non-fermentable sugars.

Within the present invention the term "enzymatic hydrolysis" is to be understood as a process wherein suitable enzymes convert polymeric sugars such as cellulose and hemicellulose into hexose (i.e. glucose) and/or pentose (i.e. xylose) monomers.

Within the present invention the term "pretreatment" is to be understood as a process leading to at least partial removal and separation of hemicellulose from cellulose and disruption and removal of the lignin sheath, in order to decrease the crystallinity of cellulose and thus to increase the accessible surface area of cellulose and/or to increase the pore size of cellulose.

The pretreatment preferentially mobilises the pentose fraction of the lignocellulose-containing material, while at the same time it enhances the digestibility of the solid cellulose-containing fraction.

Methods suitable for the pretreatment of the lignocellulose-containing material according to step (a) of the present invention include any kind of mechanical, biological, chemical and/or physical pretreatment methods known to a person skilled in the art. Within a preferred embodiment, the pretreatment method is selected from the methods of mechanical comminution, treatment with acids and/or alkalines, wet oxidation, pH-controlled hydrothermolysis and/or steam explosion.

"Steam explosion" according to the present invention preferably comprises a pressurised hydrothermal treatment at a temperature of from 60 to 350° C., preferably from 80 to 300° C., particularly preferred from 100 to 250° C. and most preferred from 110 to 220° C. of the lignocellulose-containing material in the absence or presence of acid (such as $H_2SO_4$, HCl, $H_3PO_4$) or base/alkaline (i.e. $NH_4OH$, NaOH, KOH, lime) catalysts, which are added at concentrations from 0.01 to 15% (wt./wt.), preferably from 0.05 to 12.5% (wt./wt.), more preferred from 0.1 to 10% (wt./wt.) and most preferred from 0.25 to 7.5%. In a preferred embodiment of the present invention the pressure is preferably selected from 1 to 100 bar, preferably from 2 to 50 bar, also preferred from 3 to 25 bar and most preferred from 5 to 15 bar. Reaction times during steam explosion have to be selected from 10 s to 2 h, preferably from 1 minute to 1.5 hours, and most preferred from 5 minutes to 1 hour to provide for efficient transformation of the biomass components in preparation for enzymatic hydrolysis. Within a particularly preferred embodiment a "mechanical comminution" pretreatment of the lignocellulose-containing material is carried out before or during the steam explosion pretreatment, wherein the mechanical comminution is selected from the group consisting of mechanical processing, grinding, chopping, crushing, cutting, irradiation, milling and combinations thereof.

"Acid pretreatment" according to the present invention preferably constitutes a continuous dilute and/or mild acid treatment, such as, treatment with sulfuric acid, or another organic acids, such as acetic acid, citric acid, tartaric acid, succinic acid, hydrogen chloride or mixtures thereof. Other acids may also be used. A "mild acid treatment" according to the present invention is to be understood as carried out at a pH of from 1 to 5, preferably pH from 2 to 3 (respective to the lignocellulose-containing material). In a preferred embodiment the acid is added in concentrations from 0.01 to 15 wt.-% (wt./wt.), preferably from 0.05 to 12.5 wt.-% (wt./wt.), more preferred from 0.1 to 10 wt.-% (wt./wt.) and most preferred from 0.25 to 7.5 wt.-%. The acid is preferably sulfuric acid. The acid may be contacted with the lignocellulose-containing material at a temperature in the range of from 120 to 280° C., preferably from 135 to 225° C. and most preferred from 150 to 200° C. for a period from 1 to 60 minutes, preferably 2 to 30 minutes and most preferred from 5 to 15 minutes. Addition of strong acids, such as sulphuric acid, may be applied within particularly preferred embodiments to remove hemicellulose.

"Chemical pretreatment" according to the present invention also pertains to treatment of the lignocellulose-containing material with $H_2O_2$, ozone, Lewis acids, $FeCl_3$, $(Al)_2SO_4$ in aqueous alcohols, glycerol, dioxane, phenol, ethylene glycol, NaOH, $Na_2CO_3$ and/or ammonia. Preferred concentrations, temperature and duration are chosen analogous to the conditions referenced above regarding acid pretreatment.

"Wet oxidation pretreatment" according to the present invention involves the use of oxidizing agents, such as sulphite based oxidizing agents.

The term "mechanical comminution" refers to any mechanical treatment which promotes the separation and/or release of cellulose, hemicellulose and/or lignin from lignocellulose-containing material. Mechanical comminution is preferably selected from the group consisting of mechanical processing, grinding, chopping, crushing, cutting, irradiation, milling such as dry milling, wet milling and vibratory ball milling, and combinations thereof.

"Biological pretreatment" according to the present invention refers to any biological pretreatment which promotes the separation and/or release of cellulose, hemicellulose, and/or lignin from the lignocellulose-containing material. Biological pretreatment techniques can involve applying lignin-solubilizing microorganisms such as actinomycetes (e.g. *Streptomyces* strains), white rod fungi.

Pretreatment methods suitable for the process of the present invention are to be carried out within suitable devices known to a person skilled in the art. A device suitable for carrying out chemical pretreatment may be any kind of vessel such as a batch reactor. A device suitable for carrying out steam explosion may be any kind of vessel such as a batch reactor but may also be carried out within a screw reactor, preferably a continuous screw reactor.

In a preferred embodiment the solids content of the pretreated lignocellulose-containing material is up to 75% (wt./wt.), preferably from 25 to 65% (wt./wt.) and particularly preferred from 40 to 55% (wt./wt.).

Within the process of the present invention, the pretreated lignocellulose-containing material is then contacted with at least one enzyme belonging to the class of hydrolases to decompose the pretreated lignocellulose-containing material into fermentable sugars such as monomeric hexoses (i.e. glucose) and pentoses (i.e. xylose) sugars. The contacting can be carried out by any method known to a person skilled in the art as suitable for the inventive purpose.

The hydrolyzate formed by enzymatic hydrolysis of the pretreated lignocellulose-containing material is preferably of high fermentable sugar content, preferentially being in the order of from 5 to 20% (wt./vol.). Sugar content in this context is to be understood as the content of all pentoses and hexoses. In a preferred embodiment of the invention the hydrolyzate has a sugar content of from 8 to 12.5% (wt./vol.). In a more preferred embodiment of the invention, the hydrolyzate also contains additional nutrients (i.e. proteins, salts and higher sugars such as oligosaccharides).

The contacting according to step (b) of the present invention is preferably carried out under conditions where total enzyme dosing comprises from 0.05 to 10% (wt./wt.) feedstock, preferred from 0.1 to 5% (wt./wt.) feedstock, further preferred from 0.15 to 4% (wt./wt.) feedstock and particularly preferred 0.2 to 3.5% (wt./wt.) feedstock. Depending on dosing regime and the specific activity composition of the applied enzyme system, biomass is hydrolysed at 40 to 60° C. for 1 to 7 days, preferably at from 45 to 55° C. for 18 to 96 hours. The contacting according to step (b) of the present invention is preferably carried out at a pH in the range from 3 to 8, preferably at a pH from 4 to 6, especially at a pH from 4.5 to 5.5. In a particularly preferred embodiment of this invention batch or fed-batch hydrolysis of pretreated cereal straw is accomplished at enzyme dosings of 0.25-0.8% (wt./wt.) feedstock with or without additional beta-glucosidase supplementation and at a temperature of 47 to 53° C. within 72 hours. Surprisingly even with low enzyme dosing regimes hydrolysis yields above 70% (wt./wt.) with respect to the total sugars contained in said feedstock could be obtained.

The contacting according to step (b) of the present invention is carried out within a hydrolysis vessel. Suitable vessels are known to a person skilled in the art and preferably selected from batch and fed-batch reactors.

Within the present invention, the term "enzymes belonging to the class of hydrolases" is to be understood as comprising any enzyme, capable of the hydrolysis of a chemical bond. Enzymes belonging to the class of hydrolases are classified as EC 3 in the EC number classification of enzymes. In a preferred embodiment enzymatic activities of the at least one enzyme belonging to the class of hydrolases according to the present invention comprise one or more activities selected from the activities of exo- and endocellulases (i.e. Cellobiohydrolase (CBH) I, II, endoglucanase (EG) I-IV, beta-Glucosidase (BGL)), exo- and endohemicellulases (i.e. xylanase, xylosidase, xylobiase, arabinase, arabinofucosidase, mannanase, mannosidase, galactase and galactosidase) and esterases. Within a preferred embodiment the at least one enzyme belonging to the class of hydrolases according to the present invention has one or more activities selected from the group consisting of: Cellobiohydrolase type I or type II (CBH I or CBH II), endoglucanase type I, II, III or IV (EGI, EGII, EGIII, EGIV), beta-glucosidase (BGL), esterase, exo-hemicellulase and endo-hemicellulase. Even more preferred is that the exo-hemicellulase and endo-hemicellulase are preferentially selected from xylanase, xylosidase, xylobiase, arabinase, arabinofucosidase, mannanase, mannosidase, galactase and galactosidase.

According to step (c) of the process of the present invention, the hydrolyzate is then separated from the hydrolysis vessel and subsequently divided into two parts (i) and (ii). The separation is preferably carried out when at least 70% of the total sugars present in the original feedstock are released, preferred at least 75% and most preferred at least 80%. Within a preferred embodiment, the ratio of part (i) of the hydrolyzate to part (ii) is selected from the range of from 0.01 to 1, preferably from 0.02 to 0.5, also preferred from 0.04 to 0.25 and most preferred 0.05 to 0.1.

The separation according to step (c) of the process of the present invention can be carried out by any method known to a person skilled in the art as suitable for the inventive purpose. Within a preferred embodiment, the separation is carried out by solid-liquid-separation, such as filtration, pressing, membrane separation, flotation, precipitation, decantation and centrifugation or combinations thereof. Preferred are filter-based solid-liquid separations. It is further particularly preferred to use a filter press. The residues after the filtration should have a minimal solid content of 20% (wt./wt.), preferably 30% (wt./wt.), particularly preferred 40% (wt./wt.) and most preferred 50% (wt./wt.) solid content. Another method for the separation according to step (c) is centrifugation by e.g. using a decanter.

According to step (c) of the process of the present invention, part (i) of the hydrolyzate is then directed to a cultivation vessel. Suitable vessels are known to a person skilled in the art and preferably selected from batch and fed-batch reactors. The cultivation vessel is preferably equipped with a stirrer and an aeration device. Within another preferred embodiment of the present invention part of the pretreated lignocellulose-containing material can be added directly to the cultivation vessel. Preferred amounts of added pretreated lignocellulose-containing material are from 1 to 35% (wt./wt. related to the total weight of the cultivation material), preferably from 5 to 30% (wt./wt. related to the total weight of the cultivation material) and most preferably from 10 to 20% (wt./wt. related to the total weight of the cultivation material).

According to step (d) of the process of the present invention, part (i) of the hydrolyzate is then fermented with at least one microorganism capable of the production of at least one enzyme belonging to the class of hydrolases.

The "at least one microorganism capable of the production of at least one enzyme belonging to the class of hydrolases" is preferably selected from the following species *Actinobacter* sp., *Agrobacterium* sp., *Bacillus* sp., *Burkholdria* sp., *Clostridia* sp., *Caldicellulosiruptor* sp., *Cellvibrio* sp., *Halobacterium* sp., *Pseudomonas* sp., *Paenibacillus* sp., *Xanthomonas* sp. and *Thermobifida* sp., *Pyrochoccus* sp., *Sulphobolus* sp., *Staphylothermus* sp. and *Thermococcus* sp.

The "at least one fungus capable of the production of at least one enzyme belonging to the class of hydrolases" is preferably selected from the following species *Trichoderma* sp., *Hypocrea* sp., *Aspergillus* sp., *Chaetomium* sp., *Chrysosporium* sp., *Fusarium* sp., *Humicola* sp., *Orpinomyces* sp., *Pencillium* sp., *Phanerochaete* sp., *Piromyces* sp., *Talaromyces* sp., *Trametes* sp. and *Trichoderma* sp. or their respective holomorphs. Especially preferred is a fungus selected from *Trichoderma* sp. and *Talaromyces* sp., whereas combinations of one or more fungi, but also combinations of one ore more fungi and/or microorganisms are also possible.

In a preferred embodiment of the present invention, the enzyme production is achieved with a cellulase hyperproducing strain of the filamentous fungus *Trichoderma reesei* (anamorph: *Hypocrea jecornia*).

Fermentation according to step (d) of the process of the present invention is carried out for a time period from 1 hour to 14 days, preferably from 10 hours to 7 days, further preferred from 24 hours to 5 days, preferably under constant mixing with a power input from 150 to 1900 W/m$^3$ and more preferably from 500 to 1500 W/m$^3$ and preferably at a pH from 2.5 to 8, preferably from 3.0 to 7, particularly preferred from 3.5 to 6.0 and preferably at a temperature from 15 to 70° C., preferably from 20 to 55° C. and particularly preferred from 25 to 35° C., under oxygen controlled conditions. The average dissolved oxygen level is preferably selected from 0.01% to 80%, preferred from 0.1% to 50%, particularly preferred from 1% to 30% and most preferred from 3% to 15%. Within a particularly preferred embodiment, the dissolved Oxygen level is controlled by a stirrer or compressed air flow or internal reactor pressure or a combination of two or three of these measures.

Within a preferred embodiment, the concentration of soluble sugars during fermentation according to step (d) of the inventive process is below 10% (wt./vol.), further preferred below 8% (wt./vol.) and particularly preferred below 5% (wt./vol.). Part (i) of the hydrolyzate is preferably directed to the cultivation vessel by feeding. "Feeding" according to the present invention means the subsequent addition of part (i) of the hydrolyzate to the cultivation vessel. "Feeding rate" as used within the present invention is defined as the volume of hydrolyzate transferred to the cultivation vessel measured in m$^3$/hour. The person skilled in the art is able to select the feeding rate suitable for the particular process. The feeding of the hydrolysate is preferably carried out with a constant feeding rate or a variable feeding rate or a combination of both during step (d) of the inventive process. The feeding of the hydrolyzate is preferably carried out continuously during step (d) of the inventive process or in time intervals. Preferred intervals are—e.g. related to altogether 100 hour fermentation time—e.g. a constant feeding over 60 hours which is then brought to a stop until the end of the fermentation time of 100 hours. Another possible example is to start with constant feeding over 20 hours which is interrupted after 20 hours and resumed as soon as the fermentable sugar within the hydrolyzate has been completely fermented.

After fermentation, the fermented hydrolyzate is redirected to the hydrolysis vessel according to step (e) of the process of the present invention. The redirection according to step (e) of the process of the present invention can be carried out by any method known to a person skilled in the art as suitable for the inventive purpose. During redirection according to step (e) of the inventive process, the hydrolyzate is preferably physically, mechanically and/or chemically processed. Preferred methods of redirecting include pumping or other methods of power-requiring transporting suspensions such as inline high shear force mixing. Within a particularly preferred embodiment, the redirection is carried out by pumping the hydrolyzate to the hydrolysis vessel. Processing the hydrolyzate prior to fermentation according to step (d) of the inventive process will result in even faster hydrolysis kinetics and superior monomeric sugar yield as cell-bound enzymes are more easily released from the fungus and/or microorganism.

Depending on the applied method of pretreatment, substances inhibitory to at least one enzyme and/or at least one microorganism and/or fungus are produced during step (a) of the process of the present invention. These compounds severely decrease both the hydrolysis and fermentation rate.

The inventive process according to steps (a) to (e) as defined above does, of course, already provide various advantages regarding cost and efficiency due to integrated self-sufficient enzyme production, however, running the process in a continuous way over several days may lead to an accumulation of these inhibitory substances which will compensate some of these advantages leading to a slow down of enzyme production and/or hydrolysis. To guarantee a process for self-sufficient enzyme hydrolysis which is also attractive to be implemented in industrial scale production processes such as the subsequent production of fermentation products (e.g. bioethanol), the inventors of the present invention have surprisingly found that these risks can be prevented by removal of one or more of these substances integrated at certain process stages.

These inhibitory substances are lignocellulose degradation products including lignin degradation products, cellulose degradation products and hemicellulose degradation products. The lignin degradation products may be phenolic in nature. The hemicellulose degradation products include furans from sugars (such as hexoses and/or pentoses), including xylose, mannose, galactose, rhamnose, and arabinose. Examples of hemicelluloses include xylan, galactoglucomannan, arabinogalactan, arabinoglucuronoxylan, glucuronoxylan, and derivatives and combinations thereof. Examples of lignocellulose degradation products, include 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone, eugenol or combinations thereof.

To guarantee a most efficient process within a preferred embodiment of the process of the present invention, the at least one substance inhibitory to at least one enzyme and/or inhibitory to at least one microorganism to be removed is a substance inhibitory to at least one enzyme belonging to the class of hydrolases and/or inhibitory to at least one microorganism and/or fungus capable of the production of at least one enzyme belonging to the class of hydrolases.

Within a further particularly preferred embodiment, the substance is inhibitory to at least one fungus selected from the group consisting of *Trichoderma* sp. and *Talaromyces* sp. such as *Trichoderma reesei* and/or inhibitory to at least one microorganism selected from the group consisting of *Saccharomyces* sp., *Clostridium* sp., *Lactobacillus* sp. and *Pichia* sp.

Within a preferred embodiment of the process of the present invention these at least one substance is removed from the pretreated lignocellulose-containing material according to step (a) and/or from part (i) and/or (ii) of the hydrolyzate according to step (c).

Within further preferred embodiments, the removal is carried out by adding at least one adsorbent to the pretreated lignocellulose-containing material and/or part (i) and/or (ii) of the hydrolyzate according to step (c). The adsorbent is preferably selected from the group consisting of activated carbon, silica, silicate minerals, zeolites, charcoal, clay, ion exchange resins and mixtures thereof, whereas activated carbon and/or charcoal are particularly preferred.

It is further preferred that the at least one adsorbent is added to the pretreated lignocellulose-containing material by adding the adsorbent before the pretreated lignocellulose-containing material is transferred to the hydrolysis vessel. It is, however, also within the scope of the present invention to add the adsorbent directly to the hydrolysis vessel or to add the adsorbent just before the separation according to step c).

Removal of the at least one inhibitory compound by addition of an adsorbent provides ample advantages. On the one hand, filterability is considerably enhanced. Further, in case activated carbon or charcoal is used as an adsorbent, the combustibility of the filter cake is enhanced and no or only a minimal amount of energy has to be spent on drying. Thus, an energy-independent process can be achieved by combustion of the filter cake.

Within another preferred embodiment of the present invention, the removal of the at least one inhibitory substance from part (i) and/or (ii) of the hydrolyzate is carried out by evaporation. Due to the volatile character of most of the inhibitory substances, evaporation is another efficient method of removal. "Evaporation" according to the present invention is preferably carried out under reduced pressure, preferably pressure below atmospheric pressure, preferred below 750 mbar absolute, more preferred below 500 mbar absolute, even more preferred below 250 mbar absolute and most preferred below 125 mbar absolute. Preferred ranges are from 75 to 750 mbar absolute and from 75 to 250 mbar absolute. During evaporation, the temperature is preferably kept below 120° C., more preferred below 100° C. even more preferred below 90° C. and most preferred below 80° C. Preferred ranges are from 45 to 120° C. and from 45 to 100° C. Residence times are preferably chosen from 0.1 s to 10 h, preferred from 1 s to 1 h, more preferred from 10 s to 30 min, most preferred from 30 s to 10 min. The pH is preferably kept below pH6, more preferred below pH 5.5, even more preferred below 5.0 and most preferred below 4.8. Preferred ranges are from 3.5 to 6 and from 4.0 to 5.0. Preferred evaporators are circulation evaporators, thin film evaporators, wiped film evaporators and falling film evaporators.

Removal of the at least one inhibitory substance by evaporation provides further advantages as evaporation also provides the benefit of a sterilization of the hydrolyzate. Thus, cross-contamination during fermentation can be prevented. Further, next to most of the inhibitory substances a substantial amount of water will be evaporated leading to a concentrated hydrolyzate (i.e. decreased volume and higher sugar concentration) resulting in further cost reduction due to an increased throughput and minimized reactor volume. Evaporation is such an effective method of removal that substantial advantages of the inventive process can already be achieved by applying this methods only to part (i) of the hydrolyzate.

Within another preferred embodiment it is also possible to combine several methods of removal, wherein it is particularly preferred to combine the addition of an adsorbent before transferring the hydrolyzate to the hydrolysis vessel with evaporation applied to part (i) and/or (ii) of the hydrolyzate. Within this particular embodiment, it is also preferred to add the adsorbent before separation according to step c), particularly preferred before hydrolysis according to step b). It is particularly preferred that the process according to the invention does not comprise removal by washing the pretreated material and/or hydrolysate.

Within another preferred embodiment of the process of the present invention, an additional amount of from 0.01 to 30% (wt./vol.) of lignocellulose-containing material, preferably from 0.1 to 25% (wt./vol.), further preferred from 0.5 to 22% (wt./vol.) and particularly preferred from 1 to 20% (wt./vol.) is added to the cultivation vessel. Within a particularly preferred embodiment, the lignocellulose-containing material is obtained by separating it from the pretreatment vessel. Adding pretreated lignocellulose-containing material will lead to slow release of carbon and function as an inductor for cellulase expression.

In another aspect, the present invention is further directed to a process for the production of an organic compound from part (ii) of the hydrolyzate as defined above comprising the step (f1) contacting part (ii) of the hydrolyzate with at least one microorganism and/or fungus capable of the production of an organic compound selected from the group consisting of organic acids, amino acids, caprolactams, antibiotics, vitamins, enzymes, nucleotides/nucleosides, biogas, proteins, polysaccharides, amino glucans, organic solvents, biofuels, biosurfactants, aminoglucans, sugar derivatives and mixtures thereof;

or (f2) subjecting part (ii) of the hydrolyzate a chemical conversion, catalytic conversion, chromatographic separation, membrane separation and/or crystallisation process.

According to the process for the production of an organic compound according to step (f1) as defined above, the temperature during contacting part (ii) of the hydrolyzate with the at least one microorganism is selected from 10 to 65° C., preferably from 15 to 55° C., especially preferred from 20 to 50° C., most preferred from 25 to 45° C.

It is particularly preferred that the at least one microorganism is selected form mesophilic yeasts such as all species of genus *Saccaromyces, especially Saccharomyces bayanus, Saccharomyces boulardii, Saccharomyces bulderi, Saccha-*

*romyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum, Saccharomyces zonatus*, as well as *Arxula adeninovorans, Ashbya gossypii, Hansenula polymorpha, Debaramyces hansenii, Hortea werneckii, Kluyveromyces lactis, Schwanniomyces occidentalis, Thrichosporon domesticum, Thrichosporon montevideense, Xanthophyllomyces dendrohous, Yarowia lypolytica, Zygosaccharomyces bailii, Zygosaccharomyces rouxii, Schizosaccharomyces pombe, Pichia stipitis, Pichia segobiensis, Candida shehatae, Candida tropicalis, Candida boidinii, Candida tenuis, Pachysolen tannophilus, Hansenula polymorpha, Candidafamata, Candida parapsilosis, Candida rugosa, Candida sonorensis, Candida maltosa, Issatchenkia terricola, Kloeckera apis, Pichia barkeri, Pichia cactophila, Pichia deserticola, Pichia norvegensis, Pichia membranefaciens, Pichia mexicana* and *Torulaspora delbrueckii* and any combination thereof.

In an alternative preferred embodiment of the process for the production of an organic compound from part (ii) of the hydrolyzate, the at least one microorganism is selected from thermophilic microorganisms which are preferably selected from *Candida bovina, Candida picachoensis, Candida emberorum, Candida pintolopesii, Candida thermophila, Kluyveromyces marxianus, Kluyveromyces fragilis, Kazachstania telluris, Issatchenkia orientalis, Lachancea thermotolerans* and any combination thereof. Preferred thermophylic bacteria include *Clostridium thermocellum, Clostridium thermohydrosulphuricum, Clostridium thermosaccharolyticum, Thermoanaerobium brockii, Thermobacteroides acetoethylicus, Thermoanaerobacter ethanolicus, Clostridium thermoaceticum, Clostridium thermoautotrophicum, Acetogenium kivui, Desulfotomaculum nigrificans, Desulvovibrio thermophilus, Thermoanaerobacter tengcongensis, Bacillus stearothermophilus, Thermoanaerobacter mathranii* and any combination thereof.

The use of the following mesophilic yeasts is especially preferred: *Saccharomyces cerevisiae, Pichia stipitis, Pachysolen tannophilu* and/or *Candida shehatae*.

In an alternative embodiment of the process for the production of organic compounds from part (ii) of the hydrolyzate at least one fungus is used. The at least one fungus is selected from *Aspergillus* sp., *Trichoderma* sp., *Hypocrea* sp., *Penicillium* sp., *Acremonium* sp., *Rhizopus* sp., *Talaromyces* sp. and any combination thereof.

In an alternative embodiment of the process for the production of organic compounds from part (ii) of the hydrolyzate the microorganism is selected from bacteria species such as *Clostridium acetobutylicum, Lactobacillus brevis, Lactobacillus bulgaricus, Lactobacillus casei, Lactobacillus helveticus, Lactobacillus lactis, Lactococcus lactis, Leuconostoc mesenteroides, Lactobacillus* sp., *Zymomonas mobilis, Escherichoia coli* and any combination thereof.

Further, any combination of the above listed microorganisms and/or fungi is to be understood as within the scope of the present invention.

Fermentation is preferably conducted in a batch mode (discontinuous), in the fed-batch mode or in a continuous mode. Most preferably, fermentation is conducted in the batch mode.

Within a further preferred embodiment, minerals such as copper, zinc, magnesium, calcium, iron and nitrogen-containing compounds such as nitrate, amino acids, ammonia are added to part (ii) of the hydrolyzate prior to step f1) of the process for the production of an organic compound.

Valuable organic compounds resulting from bacterial fermentation of part (ii) of the hydrolyzate comprise but are not limited to organic acids (such as acetic acid, lactic acid, succinic acid, itaconic acid, fumaric acid, propionic acid, and glucuronic acid), amino acids (such as glutamic acid, leucine, lysine, threonine, aspartic acid, phenylalanine, cysteine), caprolactams (such as alpha-amino-caprolactam), antibiotics (such as bleomycin, virginiamycin, lincomycin, monensin, blasticidin, tetracycline), vitamins (such as vitamin B2, B12 and C), enzymes, nucleotides/nucleosides (such as NADH, ATP, cAMP, FAD, coenzyme A), biogas, biopolymers (such as polyhydroxybutyrate, polyamides/fibroins), proteins, polysaccharides (such as xanthan, dextran), amino glucans (such as hyaluronic acid) as well as organic solvents and biofuels (such as acetone, ethanol, butanol, propanediol).

Valuable organic compounds resulting from yeast fermentation of part (ii) of the hydrolyzate comprise but are not limited to organic solvents (e.g. ethanol, propanol), nucleotides (e.g. RNA), biosurfactants (e.g. sophorose lipids), enzymes, and biopolymers (e.g. spidroins).

Valuable organic compounds resulting from fungal fermentation of part (ii) of the hydrolyzate comprise organic acids (such as citric acid, fumaric acid, itaconic acid), antibiotics (such as penicillin, cephalosporin), enzymes, and polysaccharides (such as chitin).

In a further preferred embodiment of this process the organic compound is selected from alcohols, organic acids, biopolymers, antibiotics, amino acids, caprolactams, polysaccharides, organic solvents, biofuels, aminoglucans, nucleotides/nucleosides, vitamins, biosurfactants, enzymes and mixtures thereof.

According to the process for the production of an organic compound according to step (f2) subjecting part (ii) of the hydrolyzate to a chemical conversion, catalytic conversion, chromatographic separation, membrane separation and/or crystallisation process is carried out by chromatographic methods and/or filtration steps for use of purified sugars in fermentation (e.g. polymers based on lactic acid) and/or chemical conversion (production of FDCA).

In another aspect, the present invention also pertains to an organic compound produced according to the process as defined above.

In the following particularly preferred embodiments of the present invention are described and are not to be understood as limiting the invention in any respect.

Particularly Preferred Embodiment 1

Process for self-sufficient enzymatic hydrolysis of lignocellulose-containing material, comprising the steps
  (a) subjecting a lignocellulose-containing material to a pretreatment in a pretreatment device;
  (b) contacting the pretreated lignocellulose-containing material of step a) with at least one enzyme belonging to the class of hydrolases in a hydrolysis vessel to form a hydrolyzate;
  (c) separating the hydrolyzate and subsequently dividing the hydrolyzate into two parts (i) and (ii), wherein part (i) is directed to a cultivation vessel;
  (d) fermenting part (i) of the hydrolyzate with at least one microorganism and/or fungus capable of the production of at least one enzyme belonging to the class of hydrolases;

and
   (e) redirecting the fermented hydrolyzate of step d) to the hydrolysis vessel of step b);
   wherein the pretreated lignocellulose-containing material is treated to remove at least one substance inhibitory to at least one enzyme and/or at least one microorganism and/or fungus by addition of at least one adsorbent preferably selected from activated carbon, charcoal and mixtures thereof.

Particularly Preferred Embodiment 2

Process for self-sufficient enzymatic hydrolysis of lignocellulose-containing material, comprising the steps
   (a) subjecting a lignocellulose-containing material to a pretreatment in a pretreatment device;
   (b) contacting the pretreated lignocellulose-containing material of step a) with at least one enzyme belonging to the class of hydrolases in a hydrolysis vessel to form a hydrolyzate;
   (c) separating the hydrolyzate and subsequently dividing the hydrolyzate into two parts (i) and (ii), wherein part (i) is directed to a cultivation vessel;
   (d) fermenting part (i) of the hydrolyzate with at least one microorganism and/or fungus capable of the production of at least one enzyme belonging to the class of hydrolases;
   and
   (e) redirecting the fermented hydrolyzate of step d) to the hydrolysis vessel of step b);
   wherein part (i) and/or part (ii) of the hydrolyzate is treated to remove at least one substance inhibitory to at least one enzyme and/or at least one microorganism and/or fungus by evaporation.

Particularly Preferred Embodiment 3

Process for self-sufficient enzymatic hydrolysis of lignocellulose-containing material, comprising the steps
   (a) subjecting a lignocellulose-containing material to a pretreatment in a pretreatment device;
   (b) contacting the pretreated lignocellulose-containing material of step a) with at least one enzyme belonging to the class of hydrolases in a hydrolysis vessel to form a hydrolyzate;
   (c) separating the hydrolyzate and subsequently dividing the hydrolyzate into two parts (i) and (ii), wherein part (i) is directed to a cultivation vessel;
   (d) fermenting part (i) of the hydrolyzate with at least one microorganism and/or fungus capable of the production of at least one enzyme belonging to the class of hydrolases;
   and
   (e) redirecting the fermented hydrolyzate of step d) to the hydrolysis vessel of step b);
   wherein the pretreated lignocellulose-containing material is treated to remove at least one substance inhibitory to at least one enzyme and/or at least one microorganism and/or fungus by addition of at least one adsorbent preferably selected from activated carbon, charcoal and mixtures thereof and part (i) and/or part (ii) of the hydrolyzate is treated to remove at least one substance inhibitory to at least one enzyme and/or at least one microorganism and/or fungus by evaporation.

Particularly Preferred Embodiment 4

Process according to particularly preferred embodiment 1, 2 or 3, wherein the ratio of part (i) of the hydrolyzate to part (ii) is from 0.01 to 1, preferably from 0.02 to 0.5 and most preferred 0.05 to 0.1.

Particularly Preferred Embodiment 5

Process according to particularly preferred embodiment 1, 2, 3 or 4, wherein an additional amount of from 0.01 to 30% (wt./vol.) of lignocellulose-containing material, preferably from 0.15 to 25% (wt./vol.), further preferred from 0.51 to 22% (wt./vol.) and particularly preferred from 15 to 20% (wt./vol.) added to the cultivation vessel. It is most preferred within this embodiment that the lignocellulose-containing material is pretreated lignocellulose-containing material, preferably obtained from the pretreatment device.

Particularly Preferred Embodiment 6

Process according to any of particularly preferred embodiments 1 to 5, wherein the at least one microorganism capable of the production of the at least one enzyme belonging to the class of hydrolases is selected from exo- and endocellulases, beta-Glucosidase (BGL)), exo- and endohemicellulases and esterases and/or the at least one fungus capable of the production of the at least one enzyme belonging to the class of hydrolases is selected from Trichoderma and Talaromyces species and mixtures thereof and is most preferably Trichoderma reesei.

Particularly Preferred Embodiment 7

Process according to any of particularly preferred embodiments 1 to 6, further comprising the step
   (f1) contacting part (ii) of the hydrolyzate with at least one microorganism and/or fungus capable of the production of an organic compound selected from the group consisting of organic acids, amino acids, caprolactams, antibiotics, vitamins, enzymes, nucleotides/nucleosides, biogas, proteins, polysaccharides, amino glucans, organic solvents, biofuels, biosurfactants, aminoglucans, sugar derivatives and mixtures thereof;

EXAMPLE AND FIGURE

The present invention is further described by the following example and figure. The example and figure are for illustrative purposes only and are not to be understood as limiting the invention.

FIG. 2 shows the glucose, xylose and NaDL-lactate yield as well as the amount of acetic acid and formic acid when detoxifying the hydrolysate by evaporation

EXAMPLE 1

Figure 1:
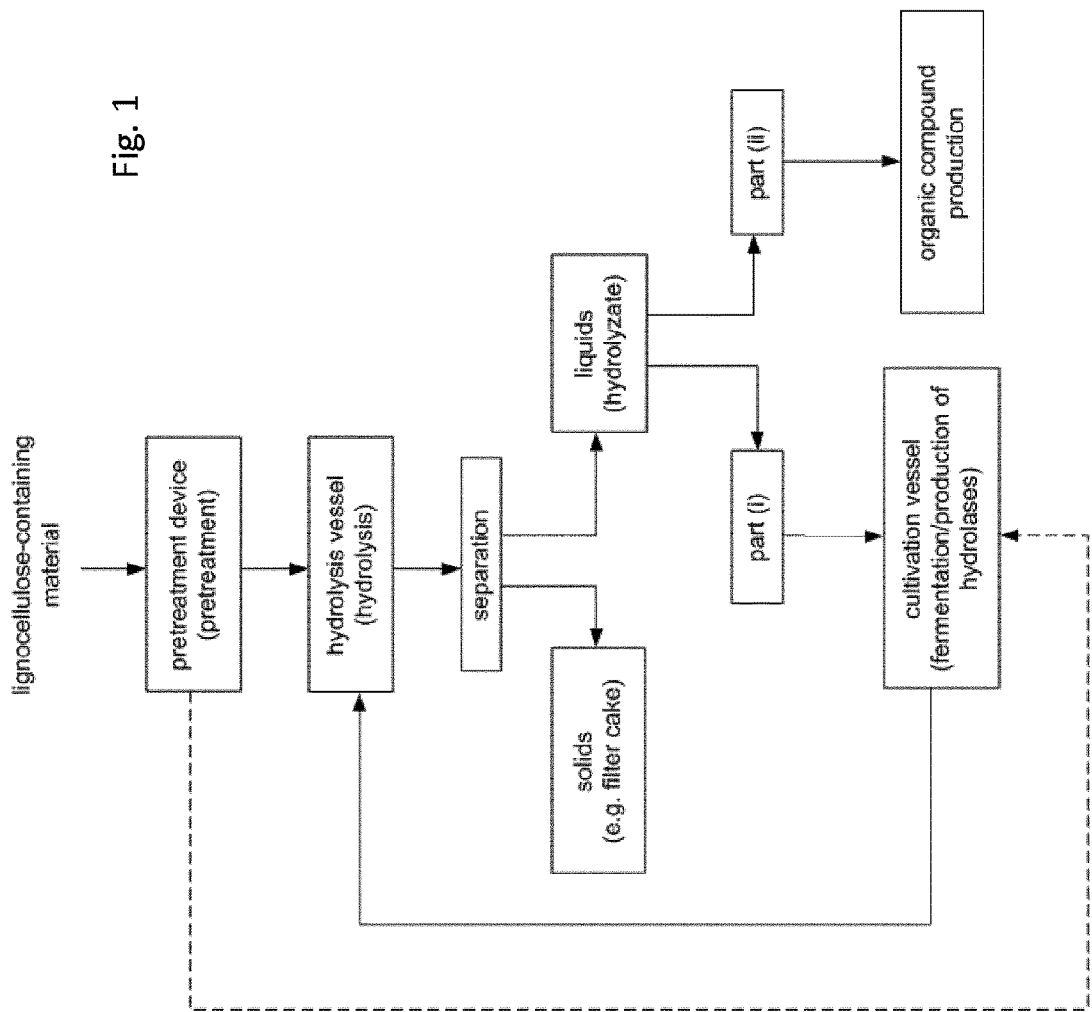
FIG. 1 shows the process flow of the process according to the present invention. The dashed line depicts the option to add part of the pretreated lignocellulose-material directly to the cultivation vessel.

Wheat Straw, Removal of Inhibitory Substance by Addition of Charcoal and Evaporation The fermentation is carried out in a stirred tank bioreactor system with a temperature, a pH- and a dissolved oxygen control device (=cultivation vessel). The cultivation is started with 5% (wt./wt.) seed culture. Furthermore, the media contains salts and minerals and concentrated hydrolyzate as main carbon source. The fermentation is carried out at pH 5, at 30° C. and at a dissolved oxygen level of 25%. Feeding of part (i) of the hydrolyzate is started after 15 hours and is carried on continuously for further 85 hours. The total feeding volume is 50% based on the total final fermentation volume.

The fermented hydrolyzate resulting from the fermentation is pumped to the pretreated wheat straw for hydrolysis of the latter.

The quantity of pretreated wheat straw present in the hydrolysis step is chosen such as that 1 m$^3$ of fermented hydrolyzate is added to 2400 kg dry matter of pretreated wheat straw.

The hydrolysis is performed at 50° C., pH 5, for 96 h with stirring at 50 rpm. After the hydrolysis, 1% (wt./vol.) activated charcoal (granulate) is added to the content of the hydrolysis vessel. The content is incubated with the activated charcoal at room temperature with stirring at 250 rpm. After 1 h, a solid-liquid separation is performed to recover the detoxified hydrolyzate by separating it from the remaining solids by centrifugation or filtration (pore size of filter <1 mm). 15% of the detoxified hydrolyzate is then subjected to an evaporation step to further remove volatile inhibitors and reduce the volume of this part of the hydrolyzate to one third of the initial volume. This double-detoxified and concentrated hydrolyzate is then introduced into the fermentation as descried above. The rest of the hydrolyzate (not undergone) evaporation can be used for the production of an organic compound.

EXAMPLE 2

Wheat Straw, Removal of Inhibitory Substance by 3-Fold Evaporation

The fermentation was carried out in a stirred tank bioreactor system with a temperature, a pH- and a dissolved oxygen control device (=cultivation vessel). The cultivation was started with 5% (wt./wt.) seed culture. Furthermore, the media contained salts and minerals and concentrated hydrolyzate as main carbon source. The fermentation was carried out at pH 5, at 30° C. and at a dissolved oxygen level of 25%. Feeding of part (i) of the hydrolyzate was started after 15 hours and was carried on continuously for further 85 hours. The total feeding volume was 45% based on the total final fermentation volume.

The fermented hydrolyzate resulting from the fermentation was pumped to the pretreated wheat straw for hydrolysis of the latter.

The quantity of pretreated wheat straw present in the hydrolysis step was chosen such as that 1 m3 of fermented hydrolyzate was added to 2400 kg dry matter of pretreated wheat straw.

The hydrolysis was performed at 50° C., pH 5, for 96 h with stirring at 50 rpm. After the hydrolysis, the hydrolyzate was then subjected to an evaporation step to remove volatile inhibitors and to reduce the volume of the hydrolyzate by a factor of 6.4. This detoxified and concentrated hydrolyzate was then introduced into the fermentation as described above.

For evaporation, the pH was adjusted to 4 using sulfuric acid and then the evaporation was carried out at 75° C. and 100 mbar. The evaporation was stopped when a sugar concentration of 500 g/L was reached. The respective yields of glucose, xylose and NaDl and the amounts of formic and acetic acid are shown in table 1 and FIG. 2. This detoxification resulted in a reduction of acetic acid by more than 80% and of formic acid by roughly 30%. The results are shown in table 1 and FIG. 2.

TABLE 1 yields of glucose, xylose and the amounts of formic and acetic acid after evaporation

|  | Yield |
|---|---|
| Factor | 6.42 |
| pH | — |
| Yields | |
| Glucose | 103% |
| Xylose | 106% |

TABLE 1-continued yields of glucose, xylose and the amounts of formic and acetic acid after evaporation

|  | Yield |
|---|---|
| Formic Acid | 72% |
| Acetic Acid | 16% |

What is claimed is:

1. A process for self-sufficient enzymatic hydrolysis of lignocellulose-containing material, comprising the steps
   (a) subjecting a lignocellulose-containing material to a pretreatment in a pretreatment device;
   (b) contacting the pretreated lignocellulose-containing material of step a) with at least one hydrolase comprising one or more activities selected from the activities of exo- or endocellulases, exo- or endohemicellulases, and esterases in a hydrolysis vessel to form a hydrolyzate;
   (c) separating the hydrolyzate and subsequently dividing the hydrolyzate into two parts (i) and (ii), wherein part (i) is directed to a cultivation vessel;
   (d) fermenting part (i) of the hydrolyzate with at least one microorganism and/or fungus capable of the production of said hydrolase; and
   (e) redirecting the fermented hydrolyzate of step d) to the hydrolysis vessel of step b);
   wherein the hydrolyzate is treated to remove at least one substance inhibitory to at least one enzyme and/or at least one microorganism and/or fungus.

2. The process according to claim 1, wherein the at least one substance inhibitory to at least one enzyme and/or at least one microorganism and/or fungus is a substance inhibitory to hydrolase and/or inhibitory to at least one microorganism and/or fungus capable of the production of hydrolase.

3. The process according to claim 1, wherein the substance is inhibitory to at least one fungus and/or microorganism selected from the group consisting of *Trichodermasp.* (anamorph: *Hypocrea* .sp), *Saccharomyces* sp., *Clostridium* sp., *Lactobacillus* sp., *Pichia* sp. and *Talaromyces* sp.

4. The process according to claim 1, wherein the substance is removed from the pretreated lignocellulose-containing material according to step (a) and/or from part (i) and/or (ii) of the hydrolyzate according to step (c).

5. The process according to claim 1, wherein the substance is removed by adding at least one adsorbent to the pretreated lignocellulose-containing material and/or part (i) and/or (ii) of the hydrolyzate according to step (c).

6. The process according to claim 5, wherein the adsorbent is selected from the group consisting of activated carbon, silica, silicate minerals, zeolites, charcoal, clay, ion exchange resins and mixtures thereof.

7. The process according to claim 1, wherein the substance is removed from part (i) and/or (ii) of the hydrolyzate according to step (c) by evaporation.

8. The process according to claim 1, wherein an additional amount of from 0.1 to 30% (wt./vol.) of lignocellulose-containing material is added to the cultivation vessel.

9. The process according to claim 8, wherein the lignocellulose-containing material is obtained by separating it from the pretreatment vessel.

10. The process according to claim 1, wherein the ratio of part (i) of the hydrolyzate to part (ii) is from 0.01 to 1.

11. The process according to claim 1, wherein the concentration of soluble sugars during the fermentation according to step d) is below 10% (wt./vol.).

12. The process according to claim 1, further comprising the step
- (f1) contacting part (ii) of the hydrolyzate with at least one microorganism and/or fungus capable of the production of an organic compound selected from the group consisting of organic acids, amino acids, caprolactams, antibiotics, vitamins, enzymes, nucleotides/ nucleosides, biogas, proteins, polysaccharides, amino glucans, organic solvents, biofuels, biosurfactants, aminoglucans, sugar derivatives and mixtures thereof; or
- (f2) subjecting part (ii) of the hydrolyzate to a chemical conversion, catalytic conversion, chromatographic separation, membrane separation and/or crystallisation process.

13. The process according to claim 1, wherein said at least one hydrolase includes an exo- or endocellulase activity selected from the group consisting of cellobiohydrolase (CBH) I, II, endoglucanase (EG) I-IV, and beta-glucosidase (BGL) and also includes an exo- or endohemicellulase activity selected from the group consisting of xylanase, xylosidase, xylobiase, arabinase, arabinofucosidase, mannanase, mannosidase, galactase and galactosidase.

14. The process according to claim 13, wherein said at least one hydrolase includes all of the following activities: CBH I, CBH II, EG I-IV, BGL, xylanase, xylosidase, xylobiase, arabinase, arabinofucosidase, mannanase, mannosidase, galactase, and galactosidase.

* * * * *